United States Patent [19]

Ishiwatari et al.

[11] Patent Number: 5,554,649

[45] Date of Patent: Sep. 10, 1996

[54] CONTROLLING AGENT FOR FABRIC PEST INSECTS

[75] Inventors: Takao Ishiwatari, Minoo; Kazunori Tsushima, Sanda, both of Japan

[73] Assignee: Sumitomo Chemical Company, Limited., Osaka, Japan

[21] Appl. No.: 359,013

[22] Filed: Dec. 19, 1994

Related U.S. Application Data

[63] Continuation of Ser. No. 98,733, Jul. 29, 1993, abandoned.

[30] Foreign Application Priority Data

Aug. 25, 1992 [JP] Japan .................. 4-225663
Mar. 30, 1993 [JP] Japan .................. 5-071699

[51] Int. Cl.$^6$ .................................. A01N 37/08
[52] U.S. Cl. .......................... 514/530; 514/531
[58] Field of Search .......................... 514/530, 531

[56] References Cited

U.S. PATENT DOCUMENTS 4,356,187  10/1982  Martel et al. .................. 424/304

FOREIGN PATENT DOCUMENTS 0018894  11/1980  European Pat. Off. .
5690004  12/1979  Japan .
56-156238  12/1981  Japan .................. C07C 69/743

OTHER PUBLICATIONS

Friedman et al, J. Agric. Food Chem. vol. 27, No. 2, 1979 pp. 331–336.

*Primary Examiner*—Brian Burn
*Attorney, Agent, or Firm*—Sughrue, Mion, Zinn, Macpeak & Seas

[57] ABSTRACT

A controlling agent for fabric pest insects characterized by containing, as an active ingredient, a carboxylic acid ester represented by the formula (I):

$$\text{(I)}$$

wherein R represents an allyl or propargyl group, Y represents a hydrogen atom or a methyl group, and when Y is a hydrogen atom, X represents an isobutenyl, 2,2-difluorovinyl or 2-chloro-2-fluorovinyl group, and when Y is a methyl group, X represents a methyl group.

16 Claims, No Drawings

CONTROLLING AGENT FOR FABRIC PEST INSECTS

This is a Continuation of application Ser. No. 08/098,733 filed Jul. 29, 1993 (now abandoned).

The present invention relates to a controlling agent for fabric pest insects.

Hitherto, pyrethroid compounds are widely used as household insecticides effective against insanitary insects such as flies, mosquitoes and the like. Among these compounds, d-allethrin, prallethrin and the like having a cyclopentenolone ring at the alcohol moiety are used as active ingredients for mosquito coils, mats and the like. However, it is not always said that these compounds are satisfactory as a controlling agent for fabric pest insects in terms of efficacy.

As a controlling agent for fabric pest insects, there are known those containing p-dichlorobenzene, naphthalene, camphor, etc. as an active ingredient are already known. These compounds, however, have problems in that the offensive odor soaks into clothes and the pest-controlling activity is not always satisfactory. On the other hand, empenthrin has recently been developed as a pyrethroid compound usable as a controlling agent for fabric pest insects. Empenthrin has the advantage that the offensive odor does not soak into clothes. Under severe conditions, however, a color change due to this compound is sometimes observed on portions of clothing which are dyed with copper, copper alloy or copper-containing dyes, so that this compound also may not always be said to be perfect as a controlling agent for fabric pest insects.

Generally, it can be said, that it is to be desirable for a controlling agent for fabric pest insects to have the various characteristics described below. That is, the properties that a controlling agent for fabric pest insects must have include, for example, the following:
1. Excellent efficacy against fabric pest insects.
2. Immediate efficacy (for prevention of feeding).
3. Long-term continuation of efficacy (long-term persistence).
4. No evolution of offensive odor even under long-term storage or severe conditions.
5. No color change even under long-term storage or severe conditions.
6. No adverse effect on clothing, for example, no color change on portions of clothing dyed with copper, copper alloy or copper-containing dyes.

In view of this situation, the present inventors have extensively studied to find a compound which is superior as a controlling agent for fabric pest insects, and as a result, they have found that a controlling agent for fabric pest insects comprising, as an active ingredient, a carboxylic acid ester represented by the formula (I):

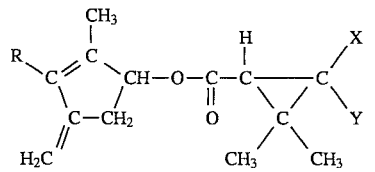

wherein R represents an allyl or propargyl group, Y represents a hydrogen atom or a methyl group, and when Y is a hydrogen atom, X represents an isobutenyl, 2,2-difluorovinyl or 2-chloro-2-fluorovinyl group, and when Y is a methyl group, X represents a methyl group, has a specifically superior performance, i.e. the above properties 1 to 6. The present inventors thus completed the present invention.

An object of the present invention is to provide a controlling agent for fabric pest insects having the above properties 1 to 6. Another object of the present invention is to provide a method for controlling fabric pest insects which comprises applying the controlling agent of the present invention to a locus where the insects inhabit. Other objects and advantages of the present invention will become apparent from the following description.

According to the present invention, there is provided a controlling agent for fabric pest insects comprising as an active ingredient, a carboxylic acid ester represented by the formula (I):

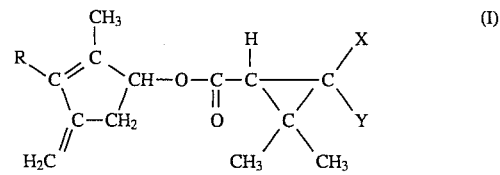

wherein R represents an allyl or propargyl group, Y represents a hydrogen atom or a methyl group, and when Y is a hydrogen atom, X represents an isobutenyl, 2,2-difluorovinyl or 2-chloro-2-fluorovinyl group, and when Y is a methyl group, X represents a methyl group.

Fabric pest insects which can be controlled with the controlling agent for fabric pest insects of the present invention include the following:

Tinea genus: *Tinea translucens* (casemaking clothes moth), etc.

Tineola genus: *Tineola bisselliella* (common clothes moth), etc.

Attagenus genus: *Attagenus unicolor* (black carpet beetle), etc.

*Attagenus piceus* (black carpet beetle), etc.

Anthrenus genus: *Anthrenus verbasci* (varied carpet beetle), etc.

Hofmannophila genus: *Hofmannophila pseudospretella* (brown house moth), etc.

Endrosis genus: *Endrosis sarcitrella* (while-shouldered house moth), etc.

| Dermestes genus: | (hide beetles) |
|---|---|
| | *D. maculatus* (hide beetles) |
| | *D. lardarius* (larder beetle) |
| | *D. haemorrhoidalis* |
| | *D. peruvianus*, etc. |

The carboxylic acid ester of the formula (I) used as an active ingredient in the present invention can be produced, for example, by the methods described in Japanese Patent Applications Kokai No. 56-156238 and U.S. Pat. No. 4,356,187 (published on Oct. 26, 1982). This carboxylic acid ester has geometrical and/or optical isomers, and these isomers and their mixtures also are included in the scope of the present invention.

The carboxylic acid ester of the formula (I) used as an active ingredient in the present invention includes for example the following compounds:

(S)-2-Methyl-4-methylidene-3-(2-propynyl)cyclopent-2-enyl (1R)-cis,trans-chrysanthemate (RS)-2-Methyl-4-methylidene-3-(2-propenyl)cyclopent-2-enyl (1RS)-cis,trans-chrysanthemate (RS)-2-Methyl-4-methylidene-3-(2-propenyl)cyclopent-2-enyl (1R)-cis,trans-chrysanthemate (RS)-2-Methyl-4-methylidene-3-(2-propenyl)cyclopent-2-enyl (1R)-trans-chrysanthemate (S)-2-Methyl-4-methylidene-3-(2-propenyl)cyclopent-2-enyl (1R)-trans-chrysanthemate (S)-2-Methyl-4-methylidene-3-(2-propynyl)cyclopent-2-enyl 2,2,3,3-tetramethylcyclopropanecarboxylate (RS)-2-Methyl-4-methylidene-3-(2-propenyl)cyclopent-2-enyl 2,2,3,3-tetramethylcyclopropanecarboxylate (RS)-2-Methyl-4-methylidene-3-(2-propynyl)cyclopent-2-enyl 2,2,3,3-tetramethylcyclopropanecarboxylate (S)-2-Methyl-4-methylidene-3-(2-propenyl)cyclopent-2-enyl 2,2,3,3-tetramethylcyclopropanecarboxylate (S)-2-Methyl-4-methylidene-3-(2-propynyl)cyclopent-2-enyl (1R)-trans-chrysanthemate (S)-2-Methyl-4-methylidene-3-(2-propenyl)cyclopent-2-enyl (1R)-trans-3-(2-chloro-2-fluorovinyl)-2,2-dimethylcyclopropanecarboxylate (S)-2-Methyl-4-methylidene-3-(2-propynyl)cyclopent-2-enyl (1R)-trans-3-(2,2-difluorovinyl)-2,2-dimethylcyclopropanecarboxylate (S)-2-Methyl-4-methylidene-3-(2-propenyl)cyclopent-2-enyl (1R)-trans-3-(2,2-difluorovinyl)-2,2-dimethylcyclopropanecarboxylate (S)-2-Methyl-4-methylidene-3-(2-propenyl)cyclopent-2-enyl (1R)-cis,trans-3-(2,2-difluorovinyl)-2,2-dimethylcyclopropanecarboxylate (S)-2-Methyl-4-methylidene-3-(2-propenyl)cyclopent-2-enyl (1R)-cis,trans-chrysanthemate (RS)-2-Methyl-4-methylidene-3-(2-propynyl)cyclopent-2-enyl (1R)-cis,trans-chrysanthemate (RS)-2-Methyl-4-methylidene-3-(2-propynyl)cyclopent-2-enyl (1RS)-trans-chrysanthemate (S)-2-Methyl-4-methylidene-3-(2-propynyl)cyclopent-2-enyl (1RS)-trans-chrysanthemate (RS)-2-Methyl-4-methylidene-3-(2-propynyl)cyclopent-2-enyl (1R)-trans-3-(2,2-difluorovinyl)-2,2-dimethylcyclopropanecarboxylate (S)-2-Methyl-4-methylidene-3-(2-propynyl)cyclopent-2-enyl (1R)-cis,trans-3-(2,2-difluorovinyl)-2,2-dimethylcyclopropanecarboxylate (RS)-2-Methyl-4-methylidene-3-(2-propynyl)cyclopent-2-enyl (1R)-cis,trans-3-(2,2-difluorovinyl)-2,2-dimethylcyclopropanecarboxylate (S)-2-Methyl-4-methylidene-3-(2-propynyl)cyclopent-2-enyl (1RS)-trans-3-(2-chloro-2-fluorovinyl)-2,2-dimethylcyclopropanecarboxylate (S)-2-Methyl-4-methylidene-3-(2-propynyl)cyclopent-2-enyl (1R)-cis,trans-3-(2-chloro-2-fluorovinyl)-2,2-dimethylcyclopropanecarboxylate (RS)-2-Methyl-4-methylidene-3-(2-propynyl)cyclopent-2-enyl (1R)-cis,trans-3-(2-chloro-2-fluorovinyl)-2,2-dimethylcyclopropanecarboxylate (RS)-2-Methyl-4-methylidene-3-(2-propynyl)cyclopent-2-enyl (1RS)-cis,trans-chrysanthemate (S)-2-Methyl-4-methylidene-3-(2-propynyl)cyclopent-2-enyl (1RS)-cis,trans-chrysanthemate (S)-2-Methyl-4-methylidene-3-(2-propynyl)cyclopent-2-enyl (1RS)-trans-3-(2,2-difluorovinyl)-2,2-dimethylcyclopropanecarboxylate (RS)-2-Methyl-4-methylidene-3-(2-propynyl)cyclopent-2-enyl (1R)-trans-chrysanthemate (S)-2-Methyl-4-methylidene-3-(2-propynyl)cyclopent-2-enyl (1R)-trans-3-(2-chloro-2-fluorovinyl)-2,2-dimethylcyclopropanecarboxylate In using the controlling agent for fabric pest insects of the present invention, the above active ingredient compounds may be applied, as they are, to places where the pest-controlling effect is required (for example, various items of furniture used for storing clothing and clothes such as Japanese bureaus, wardrobes, commodes, clothes boxes, etc.). Usually, however, the active ingredient compounds are formulated, for example, into powdery, granular, tablet-like, rod-like or plate-like solid formulations, or into liquid formulations such as emulsifiable concentrates, dispersion formulations, suspension formulations, spray formulations, aerosols, oil sprays and the like, using suitable carriers and other auxiliaries for formulation. These formulations are applied to the above places by the methods suited to their forms.

The carrier (diluent) which can be used to prepare the above liquid formulations, includes, for example, water, alcohols (e.g. methyl alcohol, ethyl alcohol), esters (e.g. ethyl acetate), halogenated hydrocarbons (e.g. dichloroethane), ketones (e.g. acetone, methyl ethyl ketone), ethers (e.g. tetrahydrofuran, dioxane), aliphatic hydrocarbons (e.g. hexane, kerosene, paraffin, petroleum benzine), aromatic hydrocarbons (e.g. benzene, toluene) and the like.

The liquid formulation can be blended with common auxiliaries for formulation such as surface active agents (emulsifiers or dispersing agents), spreading agents, wetting agents, stabilizing agents, propellants, film-forming agents (in the form of paints, adhesives, etc.) and the like. The auxiliaries for formulation include surface active agents such as soaps, polyoxyethylene fatty alcohol ethers (e.g. polyoxyethylene oleyl ether), polyoxyethylene alkylaryl ethers (e.g. polyoxyethylene nonylphenyl ether), polyoxyethylene fatty acid esters, fatty acid glycerides, sorbitan fatty acid esters, sulfuric acid esters of higher alcohols, alkylarylsulfonates (e.g. sodium dodecylbenzenesulfonate), etc.; propellants such as liquefied petroleum gas (LPG), dimethyl ether, fluorocarbons, etc.; various film-forming agents such as cellulose derivatives (e.g. nitrocellulose, acetylcellulose, methylcellulose, acetylbutylcellulose), vinyl resins (e.g. vinyl acetate resin), alkyd resins, urea resins, epoxy resins, polyester resins, urethane resins, silicone resins, acrylic resins, rubbers (e.g. chlorinated rubber), polyvinyl alcohol, etc.; and casein, gelatin, alginic acid, carboxymethyl cellulose (CMC), etc.

The carrier used in preparing the above solid formulations includes, for example, various mineral powders such as silicates, kaolin, activated carbon, bentonite, diatomaceous earth, talc, clay, calcium carbonate, ceramics powders, etc. and clathrate compounds such as cyclodextrin, etc.

Further, in the above solid formulations are also included molded products of a resin in which the active ingredient compound has been kneaded into plastics.

The controlling agent for fabric pest insects of the present invention having various forms thus obtained contains the active ingredient compound in an amount ranging usually from 0.01 to 80 wt. %, more preferably 0.1 to 65 wt. %.

To the controlling agent for fabric pest insects of the present invention may be added if necessary synergists and stabilizing agents incorporated into known pyrethroid insecticides. The synergists include piperonyl butoxide, MGK-264 [N-(2-ethylhexyl)bicyclo[2.2.1]hept-5-ene-2,3-dicarboximide], S-421 [bis(2,3,3,3-tetrachloropropyl) ether], etc., and the stabilizing agents include organic acids, phenolic antioxidants, etc. The amounts of these compounds added is usually $\frac{1}{100}$ to 10 times by weight that of the active ingredient compound. Other usable additives include volatile anti-bacterial agents, volatile anti-molding agents, coloring agents, perfumes and the like.

The controlling agent for fabric pest insects of the present invention can also be used in mixture with known controlling agents for fabric pest insects.

The controlling agent for fabric pest insects of the present invention can be applied to places where the pest-controlling effect is required, for example, furniture used for storing clothing and clothes. In this case, the controlling agent for fabric pest insects may previously be wrapped in suitable packaging, such as known various napped, crepe, net-like or laminated papers, non-woven cloths, cloths and the like, or may directly be added by means such as throwing-in, scattering, spraying, coating, sticking and the like, without being wrapped. In particular, since the active ingredient compounds of the present invention are substantially odorless, the controlling agent for fabric pest insects of the present invention can also be applied so as to be brought into direct contact with clothing and clothes.

Further, the controlling agent for fabric pest insects of the present invention can also be applied to desired places by previously fixing it to a suitable sheet-like substrate by means such as coating, impregnation, spraying, dropping, kneading and the like. The sheet-like substrate which can be used in this case includes, for example, synthetic resin sheets made of polyethylene, polypropylene, nylon, polyvinyl chloride, polyvinylidene chloride, polyester, etc.; animal, vegetable or inorganic fiber sheets (e.g. paper, cloth, non-woven cloth, leather), blended sheets or cloths made of mixtures of these synthetic resins and inorganic fibers or powders; blended cloths or non-woven cloths made of these synthetic resins and animal or vegetable fibers; and laminated sheets made of the above various sheets.

The controlling agent for fabric pest insects of the present invention can be used by previously fixing it to wood, plastic or corrugated cardboard, which are materials for furniture storing clothing and clothes, by means such as coating, impregnation, spraying, dropping, kneading and the like. Types of usable wood include, for example, paulownia, fern tree, camphor tree, yew tree, fir tree, Saghalin fir, Japanese hemlock, Jong kong, Jelutong, Agathis, Japanese cedar, Japanese walnuts, Japanese beech, Japanese oak, zelkova tree, Japanese elm, Japanese cherry birch and the like. Usable plastics include vinyl chloride resin, chlorinated polyethylene, polyethylene, polypropylene, vinyl chloride/vinyl acetate copolymer and the like. In the above, a suitable fixing method includes, for example, a method in which the active ingredient compound and a liquid which gels, crystallizes or solidifies at room temperature are impregnated, separately or after previously mixed, into the above material for furniture under normal pressure, reduced pressure or pressure. Liquids which gel at room temperature include, for example, common gelatinating agents such as dibenzylidene-D-sorbitol. Liquids which crystallize or solidify at room temperature include, for example, acetanilide, dimethyl isophthalate, magnesium acetate, dimethyl terephthalate, maleic anhydride, lauric acid, stearyl alcohol, petroleum solid paraffin, animal and vegetable solid waxes, sodium tetraborate (decahydrate), sodium aluminum sulfate, magnesium sulfate (hexahydrate), 2,4,6-triisopropyl-1,3,5-trioxane, tricyclodecane, cyclodecane, trimethylene norbornene, disodium hydrogenphosphate (pentahydrate) and the like.

The controlling agent for fabric pest insects of the present invention is applied so that the amount of the active ingredient compound is usually 10 mg to 100 g/m$^2$.

The controlling agent for fabric pest insects of the present invention applied in this way has many advantages: It has a strong pest-controlling activity against fabric pest insects, a moderate volatility and both an immediate efficacy and a persistence; when formulated into dusts, granules or sublimation formulations, it can be volatilized effectively, if small in amount, as a controlling agent for short-term use; and further, since there is hardly any odor, it can be used odorless or with a desired sweet scent added to it; and also even clothes which are stored in a bureau for a long time can be worn immediately after being removed from the bureau.

The present invention will be illustrated more specifically with reference to the following examples.

Compounds used are shown by compound numbers in Table 1.

TABLE 1

[Structural formula with R, CH$_3$, X, Y substituents]

| Compound number | Structural formula R— | X— | Y— | Isomer Alcohol moiety | Acid moiety | Refractive index n$_D$ (°C.) |
|---|---|---|---|---|---|---|
| (1) | HC≡C—CH$_2$— | CH$_3$— | CH$_3$ | S | — | 1.5137(22) |
| (2) | HC≡C—CH$_2$— | (CH$_3$)$_2$C=CH— | H— | S | (1R)-cis,trans | 1.5177(25) |
| (3) | H$_2$C=CH—CH$_2$— | CH$_3$— | CH$_3$ | RS | — | 1.4968(22) |
| (4) | H$_2$C=CH—CH$_2$— | (CH$_3$)$_2$C=CH— | H— | RS | (1R)-cis,trans | 1.5109(23) |
| (5) | HC≡C—CH$_2$— | F$_2$C=CH— | H— | S | (1RS)-trans | 1.4972(25) |
| (6) | HC≡C—CH$_2$— | FClC=CH— | H— | S | (1R)-trans | 1.5148(24) |
| (7) | H$_2$C=CH—CH$_2$— | F$_2$C=CH— | H— | RS | (1RS)-trans | 1.4907(25) |
| (8) | H$_2$C=CH—CH$_2$— | FClC=CH— | H— | RS | (1R)-trans | 1.5110(25) |

Compounds used for comparison in test examples are shown by compound symbols in Tables 2 and 3.

TABLE 2

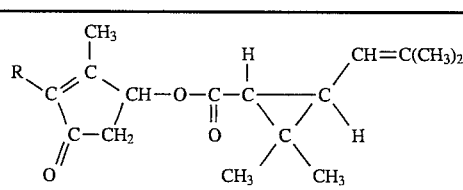

TABLE 2-continued

| Compound symbol | Structural formula R | Isomer Alcohol moiety | Isomer Acid moiety | General name |
|---|---|---|---|---|
| (A) | HC≡C—CH$_2$— | S | (1R)- | Prallethrin |
| (B) | H$_2$C=CH—CH$_2$— | RS | cis,trans (1R)- cis,trans | d-Allethrin |

TABLE 3

[Structural formula shown]

| Compound symbol | Structural formula R | Isomer Alcohol moiety | Isomer Acid moiety |
|---|---|---|---|
| (C) | HC≡C—CH$_2$— | S | (1R)-trans |
| (D) | H$_2$C=CH—CH$_2$— | RS | (1R)-trans |

The compound (C) is one described in Japanese Patent Application Kokai No. 56-156238, and the compound (D) is one described in Japanese Patent Applications Kokai No. 56-156238 and U.S. Pat. No. 4,356,187 (published on Oct. 26, 1982).

First, formulation examples will be shown.

FORMULATION EXAMPLE 1

One surface of a non-woven cloth laminated with a polyethylene film on the other surface (P.E. 80μ thick) is coated with a mixture of each of the compounds (1) to (8) with butylhydroxyanisole in a weight ratio of 5 to 1 so that the amount of each of the compounds (1) to (8) is 5 g/m². Further, a polyethylene film (thickness, 80μ) is applied to the coated surface by heat-sealing to obtain a three-layer pest-controlling sheet of each compound.

FORMULATION EXAMPLE 2

A solution of each of the compounds (1) to (8) in acetone is coated onto a kimono-wrapping paper of 0.9 m² in size so that the amount of each compound is 2 g/m², and dried to obtain a pest-controlling sheet of each compound for use in Japanese bureaus.

FORMULATION EXAMPLE 3

A solution of each of the compounds (1) to (8) in acetone is coated onto a piece of cardboard made of pulp, 100 mmφ×3 mm in size, so that the amount of each compound is 3 mg/cm², and dried to obtain a mat-like pest-controlling sheet of each compound.

FORMULATION EXAMPLE 4

A mixture comprising each of the compounds (1) to (8), silicate and cyclododecane in a weight ratio of 1:1:98 is thoroughly ground and mixed, and then formed into tablets at a rate of 10 g/tablet under a pressure of 300 kg/cm² to obtain a tablet of each compound. This tablet form is suitable for use in a non-woven cloth.

FORMULATION EXAMPLE 5

A 10% dichloromethane solution of each of the compounds (1) to (8) is applied, at a rate of 110 ml/m², onto one surface of a piece of corrugated cardboard laminated with a vinylidene chloride-coated nylon/polyethylene film on the other surface in a thickness of 20μ. Thereafter, the solvent is removed by vaporization, and a pest-controlling clothes box with a lid, 500×800×200 mm in size, of each compound is obtained.

TEST EXAMPLE 1

A filter paper (2 cm×2 cm in size) was treated with a predetermined amount of the active ingredient compound. A polyethylene cup (1) (diameter of the bottom, 10 cm; diameter of the opening, 12.5 cm; height, 9.5 cm; and volume, 950 cm³) was turned upside down, and the filter paper was hung down at a position about 2 cm below the bottom. On the bottom of another polyethylene cup of the same size (2) were put a wool muslin cloth of 2 cm×2 cm in size (about 100 mg) and ten 21 to 28-day-old larvae of the common clothes moth (*Tineola bisselliella*). The polyethylene cups (1) and (2) were fitted to each other at the respective openings and tightly sealed. After standing at 25° C. for one week, the sealed cups were opened, and the numbers of dead and alive insects and the feeding rate (weight reduction rate) of the wool muslin cloth were examined to obtain the mortality and the feeding inhibitory rate according to the following equation (four replications for each examination).

$$\text{Feeding inhibitory rate (\%)} = \frac{\text{feeding rate in untreated plot} - \text{feeding rate in treated plot}}{\text{feeding rate in untreated plot}} \times 100$$

The results obtained are shown in Table 4.

TABLE 4

| Compound | Dosage rate (μg) | Mortality (%) | Feeding inhibitory rate (%) |
|---|---|---|---|
| (1) | 100 | 100 | 100 |
| (2) | 100 | 100 | 86 |
| (3) | 100 | 100 | 100 |
| (4) | 100 | 100 | 89 |
| (5) | 100 | 100 | 97 |
| (6) | 100 | 100 | 86 |
| (7) | 100 | 100 | 95 |
| (8) | 100 | 100 | 90 |
| (A) | 400 | 0 | 10 |
| (B) | 400 | 0 | 0 |
| (C) | 200 | 70 | 64 |
| " | 100 | 60 | 44 |
| (D) | 200 | 35 | 56 |
| " | 100 | 25 | 29 |
| No treatment | — | 2.5 | 0 |

TEST EXAMPLE 2

Using the compound (1), the same test as in Test Example 1 was carried out except that larvae of the black carpet beetle (*Attagenus unicolor*) (mean body weight, 7.85 mg) were used in place of larvae of the common clothes moth (one replication).

The results are shown in Table 5.

TABLE 5

| Compound | Dosage rate (μg) | Mortality (%) | Feeding inhibitory rate (%) |
| --- | --- | --- | --- |
| (1) | 200 | 100 | 99 |
| No treatment | — | 0 | 0 |

In Test Examples 1 and 2, color change and offensive odor of the chemical-treated filter paper were not observed on any of the active ingredient compounds (1) to (8) when they were examined immediately after treatment with the compounds and one week after the treatment.

Next, color change and offensive odor of the active ingredient compounds were examined under more severe conditions.

TEST EXAMPLE 3

One hundred milligrams of each of the compounds (1) to (8) was dissolved in acetone, and the resulting acetone solution was impregnated into a filter paper, 5 cm×5 cm in size, and air-dried. The filter paper thus treated was put in a glass dish, 9 cm in diameter, and irradiated with light of 9000 to 10000 luxes from a xenon lamp for 24 hours without covering the dish with a lid. The filter paper was then taken out, and the degree of evolution of offensive odor and that of color change of the filter paper were examined.

As a result, no remarkable offensive odor nor color change was observed in any of the compounds (1) to (8).

TEST EXAMPLE 4

3.3 Milligrams of each of the compounds (1) to (8) was dissolved in acetone, and the resulting acetone solution was impregnated into a filter paper, 2 cm×1.5 cm in size, and air-dried. Separately from this, a filter paper treated with a brass powder [a filter paper, 5.5 cm in diameter, into one surface of which about 0.03 mg/cm² of a brass powder (Cu/Zn=76–78/22–24) has been rubbed] was folded in two with the brass powder-treated surface turned inwards. The above chemical-treated filter paper was held between two halves of the folded filter paper, fixed thereto with a clip and put in an aluminum-laminated bag. This bag was tightly closed by heat-sealing and kept in a constant-temperature vessel, at 60° C. for 48 hours. Thereafter, the bag was opened, and the color change and offensive odor of the brass powder-treated filter paper and chemical-treated filter paper were examined.

As a result, no clear offensive odor nor color change was observed in any of the compounds (1) to (8).

TEST EXAMPLE 5

A square filter paper (3.2 cm×3.2 cm in size) treated with a predetermined amount of the active ingredient compound was hung down at the upper central part of a corrugated cardboard box (29 cm×29 cm×29 cm in size). Three tea-strainer balls holding ten 28 to 35-day-old larvae of the common clothes moth (*Tineola bisselliella*) and one piece of wool muslin cloth of 2 cm×2 cm in size were hung down at three of the upper corners of the upper four corners of the corrugated cardboard box. The box was closed with a lid and tightly sealed. After one week, the box was opened, and the numbers of dead and alive insects, and the feeding rate (weight reduction rate) of the wool muslin cloth were examined to obtain the mortality and the feeding inhibitory rate according to the equation described above. The box was stored as it was under conditions of 25° C. and a humidity of 60% RH, and the same test was repeated 14, 32, 63 and 77 days after the treatment to examine the persistance of the compound.

The results are shown in Table 6.

TABLE 6

| Compound | Mortality (%) [feeding inhibitory rate (%)] | | | | |
| --- | --- | --- | --- | --- | --- |
|  | Immediately after | After 14 days | After 32 days | After 63 days | After 77 days |
| (1) | 100(99) | 100(99) | 100(97) | 100(99) | 100(98) |

What is claimed is:

1. A method for controlling fabric pest insects comprising applying a controlling agent which comprises an insecticidally effective amount of a carboxylic acid ester represented by the formula (I):

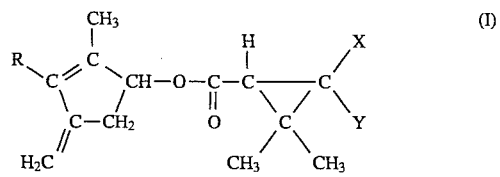

wherein R represents an allyl or propargyl group, Y is a hydrogen atom when X represents an isobutenyl, 2,2-difluorovinyl or 2-chloro-2-fluorovinyl group, and Y is a methyl group when X represents a methyl group, and an inert carrier to a locus where the insects inhabit.

2. A method according to claim 1, wherein the fabric pest insects are selected from the group consisting of Tinea, Tineola, Attagenus, Anthrenus, Hofmannophila, Endrosis and Dermestes.

3. A method according to claim 1, wherein the fabric pest insects are selected from the group consisting of *Tinea translucens, Tineola bisselliella* and *Attagenus unicolor*.

4. A method according to claims 1, 2 or 3, wherein the carboxylic acid ester is selected from the group consisting of:

(S)-2-Methyl-4-methylidene-3-(2-propynyl)cyclopent-2-enyl 2,2,3,3-tetramethylcyclopropanecarboxylate (S)-2-Methyl-4-methylidene-3-(2-propynyl)cyclopent-2-enyl (1R)-cis,trans-chrysanthemate (RS)-2-Methyl-4-methylidene-3-(2-propenyl)cyclopent-2-enyl 2,2,3,3-tetramethylcyclopropanecarboxylate (RS)-2-Methyl-4-methylidene-3-(2-propenyl)cyclopent-2-enyl (1R)-cis,trans-chrysanthemate (S)-2-Methyl-4-methylidene-3-(2-propynyl)cyclopent-2-enyl (1RS)-trans-3-(2,2-difluorovinyl)-2,2-dimethylcyclopropanecarboxylate (S)-2-Methyl-4-methylidene-3-(2-propynyl)cyclopent-2-enyl (1R)-trans-3-(2-chloro-2-fluorovinyl)-2,2-dimethylcyclopropanecarboxylate (RS)-2-Methyl-4-methylidene-3-(2-propenyl)cyclopent-2-enyl (1RS)-trans-3-(2,2-difluorovinyl)-2,2-dimethylcyclopropanecarboxylate (RS)-2-Methyl-4-methylidene-3-(2-propenyl)cyclopent-2-enyl (1R)-trans-3-(2-chloro-2-fluorovinyl)-2,2-dimethylcyclopropanecarboxylate.

5. A method according to claims 1, 2 or 3, wherein the carboxylic acid ester is (S)-2-methyl-4-methylidene-3-(2-propynyl)cyclopent-2-enyl 2,2,3,3-tetramethylcyclopropanecarboxylate.

6. A method according to claim 1, wherein the carboxylic acid ester is contained in an amount ranging from 0.01 to 80% by weight in the controlling agent.

7. A method according to claim 1, wherein the carboxylic acid ester is contained in an amount ranging from 0.1 to 65% by weight in the controlling agent.

8. A method according to claim 1, wherein the controlling agent is applied in an amount of 10 mg to 100 g/m² of the active ingredient.

9. A method according to claim 1, wherein the controlling agent is applied by volatilizing.

10. A method according to claim 1, wherein the controlling agent is applied by volatilizing at room temperature.

11. A method for protecting fabric from fabric pest insects which comprises subjecting fabric to a carboxylic acid ester represented by the formula (I):

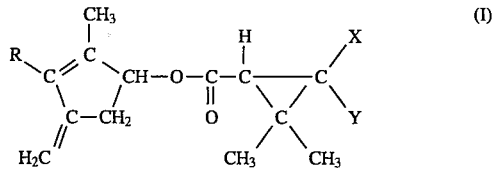

(I)

wherein R represents an allyl or propargyl group, Y is a hydrogen atom when X represents an isobutenyl, 2,2-difluorovinyl, or 2-chloro-2-fluorovinyl group, and Y is a methyl group when X represents a methyl group.

12. A method according to claim 11, wherein the step of subjecting includes volatization of the carboxylic acid ester.

13. A method according to claim 12, wherein the volatization is effected at room temperature.

14. A method according to claims 12 or 13, wherein the volatization is effected from a sheet-like substance wherein the carboxylic acid ester is fixed.

15. A method according to claim 14, wherein the sheet-like substance is one member selected from the group consisting of synthetic resin sheets, animal, vegetable or inorganic fiber sheets, blended sheets or cloths made of mixtures of synthetic resins and inorganic fibers or powders, blended cloths or non-woven cloths made of synthetic resins and animal or vegetable fibers, and laminated sheets thereof.

16. A method according to claims 12 or 13, wherein the volatization is effected from materials for furniture storing clothing and clothes wherein the carboxylic acid ester is fixed.

* * * * *